United States Patent
Falco et al.

(10) Patent No.: US 6,680,428 B2
(45) Date of Patent: Jan. 20, 2004

(54) ISOLATED NUCLEIC ACIDS ENCODING METHYLENETETRAHYDROFOLATE DEHYDROGENASE ENZYMES

(75) Inventors: Saverio Carl Falco, Wilmington, DE (US); Layo O. Famodu, Newark, DE (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/903,814

(22) Filed: Jul. 12, 2001

(65) Prior Publication Data

US 2002/0102689 A1 Aug. 1, 2002

Related U.S. Application Data

(62) Division of application No. 09/351,703, filed on Jul. 12, 1999, now abandoned.
(60) Provisional application No. 60/092,869, filed on Jul. 15, 1998.

(51) Int. Cl.$^7$ .......................... C12N 9/04; C12N 15/79; C12Q 1/32; C12P 21/06; C07H 21/04
(52) U.S. Cl. ..................... 800/295; 435/26; 435/69.1; 435/325; 435/419; 435/252.3; 435/320.1; 435/190; 435/469; 435/470; 435/410; 435/468; 536/23.2
(58) Field of Search .................. 435/26, 69.1, 468, 435/469, 470, 190, 325, 419, 252.3, 320.1, 410; 536/23.2; 800/295

(56) References Cited

PUBLICATIONS

Broun et al., Science 282:1315–1317, 1998.*
Van de Loo et al., Proc. Natl. Acad. Sci. 92:6743–6747, 1995.*
NCBI General Identifier No. 2245073, *Arabidopsis thaliana* DNA chromosome 4, ESSA I FCA contig fragment No. 8, Jul. 6, 1997.
NCBI General Identifier No. 1685109, *Streptococcus thermophilus* tetrahydrofolate dehydrogenase/cyclohydrolase (folD), penicillin–binding protein 2b (pbp2b) and DNA repair and recombination protein (recM) genes, complete cds., Nov. 27, 1996.
West et al., (1993) J. Biol. Chem., 268:153–160.
D'Ari et al. (1991) J. Biol. Chem. 266–23953–23958.
Gish and States (1993) Nature Genetics 3:266–272.
NCBI General Identifier No. 5001995, 1999.
NCBI General Identifier No. 2984098, 1998.
Nature 392, pp. 353–358, (1998).
NCBI General Identifier No. 2500006, 1997.
J. Biol. Chem. 270(31) pp. 18252–18259 (1995).
NCBI General Identifier No. 1706872, 1996.
J. Biol. Chem., 268(30), pp. 22820–22824 (1993).
NCBI General Identifier No. 4103987, 1999.
NCBI General Identifier No. U58210, 1998.
Stingele et al., Mol. Microbiol. 22(2), 357–366 (1996).
Nagy et al., J. Bacteriol. 177 (5): 1292–1298 (1995).
Shannon et al., J. Biol. Chem. 263(16)7717–7725 (1988) (MEDLINE 88227973).

* cited by examiner

Primary Examiner—Rebecca E. Prouty
Assistant Examiner—Delia Ramirez

(57) ABSTRACT

This invention relates to an isolated nucleic acid fragment encoding a tetrahydrofolate metabolism enzyme. The invention also relates to the construction of a chimeric gene encoding all or a portion of the tetrahydrofolate metabolism enzyme, in sense or antisense orientation, wherein expression of the chimeric gene results in production of altered levels of the tetrahydrofolate metabolism enzyme in a transformed host cell.

10 Claims, No Drawings

ISOLATED NUCLEIC ACIDS ENCODING METHYLENETETRAHYDROFOLATE DEHYDROGENASE ENZYMES

This application is a divisional of U.S. patent application Ser. No. 09/351,703, filed Jul. 12, 1999, now abandoned, which claims the benefit of U.S. Provisional Application No. 60/092,869, filed Jul. 15, 1998, now abandoned.

FIELD OF THE INVENTION

This invention is in the field of plant molecular biology. More specifically, this invention pertains to nucleic acid fragments encoding tetrahydrofolate metabolism enzymes in plants and seeds.

BACKGROUND OF THE INVENTION

Tetrahydrofolic acid and its derivatives $N^5,N^{10}$-methylenetetrahydrofolate, $N^5,N^{10}$-methenyltetrahydrofolate, $N^{10}$-formyltetrahydrofolate, and $N^5$-methyltetrahydrofolate are the biologically active forms of folic acid, oxidized form of tetrahydrofolate (THF). The tetrahydrofolates are coenzymes which are not enzyme-bound and are specialized cosubstrates for a variety of enzymes involved in one-carbon metabolism. Tetrahydrofolate (THF) is a 6-methylpterin derivative linked to p-aminobenzoic acid and glutamic acid residues. Its function is to transfer C1 units in several oxidation states. The C1 units are convalently attached to THF at its N5 and/or N10 positions and enter into the THF pool through the conversion of serine to glycine by serine hydroxymethyl transferase and the cleavage of glycine by glycine synthase. A C1 unit in the THF pool can have several outcomes: it may be used in the conversion of the deoxynucleotide dUMP to dTMP by thymidylate synthase, it may be reduced for the synthesis of methionine, or it may oxidized for the use in the synthesis of purines, since the purines ring of ATP is involved in histidine biosynthesis.

There are several enzymes involved in tetrahydrofolate metabolism five of which are, methylenetetrahydrofolate dehydrogenase (NADP+), 5,10-methylenetetrahydrofolate reductase, 3-methyl-2-oxobutanoate hydroxymethyltransferase, glutamate formyltransferase, or formyltetrahydrofolate deformnylase. Methylenetetrahydrofolate dehydrogenase (NADP+) is an oxidoreductase which acts on the CH—NH group of donors with NAD+ or NADP+ as acceptor. In eucaryotes it occurs as a trifunctional enzyme also having methenyltetrahydrofolate cyclohydrolase (EC 3.5.4.9) and formyltetrahydrofolate synthase (EC 6.3.4.3) activity. In some prokaryotes it occurs as a bifunctional enzyme also having methenyltetrahydrofolate cyclohydrolase activity (EC 3.5.4.9). This trifunctional enzyme consists of two major domains: an aminoterminal part, containing the methylene-THF dehydrogenase and methenyl-THF cyclohydrolase activities and a larger formyl-THF synthetase domain.

5,10-Methylenetetrahydrofolate reductase (EC 1.7.99.5) (MTHFR) plays a role in the synthesis of methionine (West et al, (1993) *J. Biol. Chem.* 268:153–160 and D'Ari et al. (1991) *J Biol. Chem.* 266:23953–23958). S-adenosylmethionine (SAM) an important methyl group donor for many biosynthetic methylation reactions in plants. SAM is formed from methionine by SAM synthetase. Transfer of the methyl group from SAM to an acceptor molecule results in the formation of S-adenosylhomocysteine, which is then hydrolyzed to homocysteine. Methionine is regenerated from homocysteine by methyl group transfer from 5-methyltetrahydrofolate. This form of folate is generated from 5,10-methylenetetrahydrofolate through the action of 5,10-methylenetetrahydrofolate reductase (MTHFR), a cytosolic flavoprotein. The heavy demand in plant cells for methyl groups derived from SAM necessitate a rapid recycling of S-adenosylhomocysteine, and thus a heavy demand for 5-methyltetrahydrofolate produced by MTHFR.

3-Methyl-2-oxobutanoate hydroxymethyltransferase (EC 2.1.2.11) is the first enzyme in the pantothenate biosynthetic pathway. This enzyme catalyses the conversion of 5,10-methylenetetrahydrofolate and 3-methyl-2-oxobutanoate to tetrahydrofolate and 2-dehydropantoate. Pantothenate is a vitamin required in the diet of animals. It is used in the synthesis of coenzyme A, which in turn, is used in many important enzyme reactions in many pathways, e.g., fatty acid biosynthesis. The production of high levels fatty acids, which require coenzyme A for their synthesis, might be stimulated by production of higher levels of coenzyme A, which in turn would require increased production of pantothenate. Another use might be for the increased production of pantothenate in plants in order to purify this vitamin for sale.

Glutamate formyltransferase (EC 2.1.2.5) catalyses the transfer of a formyl group from 5-formyltetrahydrofolate to L-glutamate. This enzyme serves to channel one-carbon units from formiminoglutamate to the folate pool.

Lastly, formyltetrahydrofolate deformylase (EC 3.5.1.10) catalyses the formation of formate and tetrahydrofolate from 10-formyltetrahydrofolate and water. 10-Formyltetrahydrofolate is required in de novo purine biosynthesis and histidine biosynthesis.

Because these enzymes are involved in tetrahydrofolate metabolism, amino acid synthesis, fatty acid biosynthesis and de novo synthesis of purines inhibition of their activity may be lethal, thus suggesting that they would be attractive herbicide targets. Thus production of these plant enzymes in bacteria for use in a high throughput screen for chemical inhibitors would be desirable. Alternatively, overproduction of these enzymes in transgenic plants could be used to enhance the production of many secondary metabolites, amino acids, purine nucleic acids and vitamins. Accordingly, the availability of nucleic acid sequences encoding all or a portion of an enzyme involved in tetrahydrofolate metabolism would facilitate studies to better understand tetrahydrofolate metabolism in plants, provide genetic tools to enhance the production of secondary metabolites, amino acids and vitamins. These enzymes may also provide targets to facilitate design and/or identification of inhibitors tetrahydrofolate metabolism that may be useful as herbicides.

SUMMARY OF THE INVENTION

The instant invention relates to isolated nucleic acid fragments encoding tetrahydrofolate metabolism enzymes. Specifically, this invention concerns an isolated nucleic acid fragment encoding a 3-methyl-2-oxobutanoate hydroxymethyltransferase, formyltetrahydrofolate deformylase, glutamate formiminotransferase or methylenetetrahydrofolate dehydrogenase and an isolated nucleic acid fragment that is substantially similar to an isolated nucleic acid fragment encoding a 3-methyl-2-oxobutanoate hydroxymethyltransferase, formyltetrahydrofolate deformylase, glutamate formiminotransferase or methylenetetrahydrofolate dehydrogenase. In addition, this invention relates to a nucleic acid fragment that is complementary to the nucleic acid fragment encoding 3-methyl-2-oxobutanoate hydroxymethyltransferase, formyltetrahydrofolate deformylase, glutamate formiminotransferase or methylenetetrahydrofolate dehydrogenase.

An additional embodiment of the instant invention pertains to a polypeptide encoding all or a substantial portion of a tetrahydrofolate metabolism enzyme selected from the group consisting of 3-methyl-2-oxobutanoate hydroxymethyltransferase, formyltetrahydrofolate deformylase, glutamate formiminotransferase and methylenetetrahydrofolate dehydrogenase.

In another embodiment, the instant invention relates to a chimeric gene encoding a 3-methyl-2-oxobutanoate hydroxymethyltransferase, formyltetrahydrofolate deformylase, glutamate formiminotransferase or methylenetetrahydrofolate dehydrogenase, or to a chimeric gene that comprises a nucleic acid fragment that is complementary to a nucleic acid fragment encoding a 3-methyl-2-oxobutanoate hydroxymethyltransferase, formyltetrahydrofolate deformylase, glutamate formiminotransferase or methylenetetrahydrofolate dehydrogenase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a 3-methyl-2-oxobutanoate hydroxymethyltransferase, formyltetrahydrofolate deformylase, glutamate formiminotransferase or methylenetetrahydrofolate dehydrogenase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a 3-methyl-2-oxobutanoate hydroxymethyltransferase, formyltetrahydrofolate deformylase, glutamate formiminotransferase or methylenetetrahydrofolate dehydrogenase in a transformed host cell comprising: a) transforming a host cell with a chimeric gene comprising a nucleic acid fragment encoding a 3-methyl-2-oxobutanoate hydroxymethyltransferase, formyltetrahydrofolate deformylase, glutamate formiminotransferase or methylenetetrahydrofolate dehydrogenase; and b) growing the transformed host cell under conditions that are suitable for expression of the chimeric gene wherein expression of the chimeric gene results in production of altered levels of 3-methyl-2-oxobutanoate hydroxymethyltransferase, formyltetrahydrofolate deformylase, glutamate formiminotransferase or methylenetetrahydrofolate dehydrogenase in the transformed host cell.

An addition embodiment of the instant invention concerns a method for obtaining a nucleic acid fragment encoding all or a substantial portion of an amino acid sequence encoding a 3-methyl-2-oxobutanoate hydroxymethyltransferase, formyltetrahydrofolate deformylase, glutamate formiminotransferase or methylenetetrahydrofolate dehydrogenase.

A further embodiment of the instant invention is a method for evaluating at least one compound for its ability to inhibit the activity of a 3-methyl-2-oxobutanoate hydroxymethyltransferase, formyltetrahydrofolate deformylase, glutamate formiminotransferase or methylenetetrahydrofolate dehydrogenase, the method comprising the steps of: (a) transforming a host cell with a chimeric gene comprising a nucleic acid fragment encoding a 3-methyl-2-oxobutanoate hydroxymethyltransferase, formyltetrahydrofolate deformylase, glutamate formiminotransferase or methylenetetrahydrofolate dehydrogenase, operably linked to suitable regulatory sequences; (b) growing the transformed host cell under conditions that are suitable for expression of the chimeric gene wherein expression of the chimeric gene results in production of 3-methyl-2-oxobutanoate hydroxymethyltransferase, formyltetrahydrofolate deformylase, glutamate formiminotransferase or methylenetetrahydrofolate dehydrogenase in the transformed host cell; (c) optionally purifying the 3-methyl-2-oxobutanoate hydroxymethyltransferase, formyltetrahydrofolate deformylase, glutamate formiminotransferase or methylenetetrahydrofolate dehydrogenase expressed by the transformed host cell; (d) treating the 3-methyl-2-oxobutanoate hydroxymethyltransferase, formyltetrahydrofolate deformylase, glutamate formiminotransferase or methylenetetrahydrofolate dehydrogenase with a compound to be tested; and (e) comparing the activity of the 3-methyl-2-oxobutanoate hydroxymethyltransferase, formyltetrahydrofolate deformylase, glutamate formiminotransferase or methylenetetrahydrofolate dehydrogenase that has been treated with a test compound to the activity of an untreated 3-methyl-2-oxobutanoate hydroxymethyltransferase, formyltetrahydrofolate deformylase, glutamate formiminotransferase or methylenetetrahydrofolate dehydrogenase, thereby selecting compounds with potential for inhibitory activity.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Tetrahydrofolate Metabolism Enzymes

| | | SEQ ID NO: | |
|---|---|---|---|
| Protein | Clone Designation | (Nucleotide) | (Amino Acid) |
| 3-Methyl-2-oxobutanoate hydroxymethyltransferase | cho1c.pk001.i4 | 1 | 2 |
| Formyltetrahydrofolate deformylase | Contig composed of: cpd1c.pk010.f6 p0127.cntbp47r p0127.cntbp48r | 3 | 4 |

TABLE 1-continued

Tetrahydrofolate Metabolism Enzymes

| Protein | Clone Designation | SEQ ID NO: (Nucleotide) | SEQ ID NO: (Amino Acid) |
|---|---|---|---|
| Formyltetrahydrofolate deformylase | r1s72.pk0011.d1 | 5 | 6 |
| Formyltetrahydrofolate deformylase | wr1.pk0075.c11 | 7 | 8 |
| Glutamate formimino-transferase | r1s6.pk0086.g2 | 9 | 10 |
| Glutamate formimino-transferase | sfl1n.pk003.o10 | 11 | 12 |
| Glutamate formimino-transferase | wre1n.pk0041.e8 | 13 | 14 |
| Methylenetetrahydrofolate dehydrogenase | Contig composed of:<br>cbn10.pk0021.f6<br>cbn2.pk0047.b3<br>cbn2n.pk0012.g11<br>cc71.pk0002.f2<br>cco1n.pk0041.d9<br>cen3n.pk0027.c12<br>cen3n.pk0128.d9<br>cr1n.pk0196.f11<br>cta1n.pk0073 g9 | 15 | 16 |
| Methylenetetrahydrofolate dehydrogenase | r1r6.pk0059.b1 | 17 | 18 |
| Methylenetetrahydrofolate dehydrogenase | ses2w.pk0009.d8 | 19 | 20 |
| Methylenetetrahydrofolate dehydrogenase | Contig composed of:<br>wdk1c.pk012.f19<br>w11.pk0006.h11<br>w1e1n.pk0031.g8<br>wr1.pk0101.c9<br>wr1.pk0118.c6<br>wre1n.pk170.f4<br>wre1n.pk170.g10 | 21 | 22 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the MEGALIGN® program of the LASERGENE® bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence often or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several tetrahydrofolate metabolism enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other 3-methyl-2-oxobutanoate hydroxymethyltransferase, formyltetrahydrofolate deformylase, glutamate formiminotransferase or methylenetetrahydrofolate dehydrogenase enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of tetrahydrofolate metabolism in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell*

56:247–253), signal sequences or sequences encoding endoplasmic reticulum localization (Chrispeels (1991) *Ann. Rev. Plant Phys. Plant Mol Biol.* 42:21–53), or nuclear localization signals (Raikhel (1992) *Plant Phys.*100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded tetrahydrofolate metabolism enzyme. An example of a vector for high level expression of the instant polypeptides in a bacterial host is provided (Example 9).

Additionally, the instant polypeptides can be used as a targets to facilitate design and/or identification of inhibitors of those enzymes that may be useful as herbicides. This is desirable because the polypeptides described herein catalyze various steps in tetrahydrofolate metabolism. Accordingly, inhibition of the activity of one or more of the enzymes described herein could lead to inhibition plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cbn2 | Corn (*Zea mays* L.) developing kernel two days after pollination | cbn2.pk0047.b3 |
| cbn2n | Corn (*Zea mays* L.) developing kernel two days after pollination* | cbn2n.pk0012.g11 |
| cbn10 | Corn (*Zea mays* L.) developing kernel (embryo and endosperm; 10 days after pollination) | cbn10.pk0021.f6 |
| cc71 | Corn (*Zea mays* L.) type II callus tissue, undifferentiated | cc71.pk0002.f2 |
| cco1n | Corn (*Zea mays* L.) cob of 67 day old plants grown in green house* | cco1n.pk0041.d9 |
| cen3n | Corn (*Zea mays* L.) endosperm stage 3 (20 days after pollination)* | cen3n.pk0027.c12<br>cen3n. pk0128.d9 |
| cho1c | Corn (*Zea mays* L.) embryo 20 days after pollination | cho1c.pk001.i4 |
| cpd1c | Corn (*Zea mays* L.) pooled BMS treated with chemicals related to protein kinases** | cpd1c.pk010.f6 |
| cr1n | Corn (*Zea mays* L.) root from 7 day seedlings grown in light* | cr1n.pk0196.f11 |
| cta1n | Corn (*Zea mays* L.) tassel* | cta1n.pk0073 g9 |
| p0127 | Corn (*Zea mays* L.) nucellus tissue, 5 days after silking* | p0127.cntbp47r<br>p0127.cntbp48r |
| r1r6 | Rice (*Oryza sativa* L.) leaf (15 days after germination) 6 hrs after infection of *Magnaporthe grisea* strain 4360-R-62 (AVR2-YAMO); Resistant | r1r6.pk0059.b1 |
| r1s6 | Rice (*Oryza sativa* L.) leaf (15 days after germination) 6 hrs after infection of *Magnaporthe grisea* strain 4360-R-67 (avr2-yamo); Susceptible | r1s6.pk0086.g2 |
| r1s72 | Rice (*Oryza sativa* L.) leaf (15 days after germination) 72 hours after infection of *Magnaporthe grisea* strain 4360-R-67 (avr2-yamo); Susceptible | r1s72.pk0011.d1 |
| ses2w | Soybean (*Glycine max* L.) embryogenic suspension 2 weeks after subculture | ses2w.pk0009.d8 |

TABLE 2-continued cDNA Libraries from Corn, Rice, Soybean and Wheat

| Library | Tissue | Clone |
|---|---|---|
| sf11n | Soybean (*Glycine max* L,) immature flower | sf11n.pk003.o10 |
| wdk1c | Wheat (*Triticum aestivum* L.) developing kernel, 3 days after anthesis | wdk1c.pk012.f19 |
| wl1 | Wheat (*Triticum aestivum* L.) leaf 7 day old seedling, light grown | wl1.pk0006.h11 |
| wle1n | Wheat (*Triticum aestivum* L.) leaf 7 day old etiolated seedling | wle1n.pk0031.g8 |
| wr1 | Wheat (*Triticum aestivum* L.) root; 7 day old etiolated seedling | wr1.pk0075.c11<br>wr1.pk0101.c9<br>wr1.pk0118.c6 |
| wre1n | Wheat (*Triticum aestivum* L.) root; 7 day old etiolated seedling | wre1n.pk0041.e8<br>wre1n.pk170.g10<br>wre1n.pk170.f4 |

*These libraries were normalized essentially as described in U.S. Pat. No. 5,482,845, incorporated herein by reference.
**Chemicals related to protein kinases were 1,2-didecanoyl rac glycerol, straurosporine, K-252, A3, H-7, olomoucine and rapamycin cDNA libraries may be prepared by any one of many methods available. For example, the cDNAs may be introduced into plasmid vectors by first preparing the cDNA libraries in UNI-ZAP® XR vectors according to the manufacturer's protocol (STRATAGENE® Cloning Systems; Stratagene Corporation, La Jolla, Calif.). The UNI-ZAP® XR libraries are converted into plasmid libraries according to the protocol provided by Stratagene Corporation. Upon conversion, cDNA inserts will be contained in the pBLUE-SCRIPT® plasmid vector. In addition, the cDNAs may be introduced directly into precut BLUESCRIPT® II SK(+) vectors (Stratagene Corporation) using T4 DNA ligase (New England Biolabs), followed by transfection into DH10B cells according to the manufacturer's protocol (GIRCO BRL Products). Once the cDNA inserts are in plasmid vectors, plasmid DNAs are prepared from randomly picked bacterial colonies containing recombinant pBLUESCRIPT® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a PERKIN-ELMER® Model 377 fluorescent sequencer.

EXAMPLE 2

Identification of cDNA Clones cDNA clones encoding tetrahydrofolate metabolism enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

EXAMPLE 3

Characterization of cDNA Clones Encoding 3-Methyl-2-oxobutanoate hydroxymethyltransferase The BLASTX search using the EST sequences from clones listed in Table 3 revealed similarity of the polypeptides encoded by the cDNAs to 3-methyl-2-oxobutanoate hydroxymethyltransferase from *Emericella nidulans* (NCBI Identifier No. gi 5001995). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Emericella nidulans* 3-Methyl-2-oxobutanoate hydroxymethyltransferase

| Clone | Status | BLAST pLog Score to (gi 5001995) |
|---|---|---|
| cho1c.pk001.i4 | EST | 70.00 |

The data in Table 4 represents a calculation of the percent identity of the amino acid sequences set forth in SEQ ID NOs:2 and the *Emericella nidulans* sequence.

TABLE 4

Percent Identity of Amino Acid Sequences Deduced From the Nucleotide Sequences of cDNA Clones Encoding Polypeptides Homologous to *Emericella nidulans* 3-Methyl-2-oxobutanoate hydroxymethyltransferase

| SEQ ID NO. | Percent Identity to (gi 5001995) |
|---|---|
| 2 | 39% |

Sequence alignments and percent identity calculations were performed using the MEGALIGN™ program of the LASERGENE® bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a 3-methyl-2-oxobutanoate hydroxymethyltransferase. These sequences represent the first corn sequences encoding 3-methyl-2-oxobutanoate hydroxymethyltransferase.

EXAMPLE 4

Characterization of cDNA Clones Encoding Formyltetrahydrofolate Deformylase

The BLASTX search using the EST sequences from clones listed in Table 5 revealed similarity of the polypeptides encoded by the cDNAs to formyltetrahydrofolate deformylase from *Aquifex aeeolicus* (NCBI Identifier No. gi 2984098) and *Corynebacterium sp.* (NCBI Identifier No. gi 2500006). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding Polypeptides Homologous to *Aquifex aeeolicus* and Corynebacterium sp. Formyltetrahydrofolate Deformylase

| Clone | Status | BLAST pLog Score |
| --- | --- | --- |
| Contig composed of:<br>cpd1c.pk010.f6<br>p0127.cntbp47r<br>p0127.cntbp48r | Contig | 33.30 (gi 2984098) |
| r1s72.pk0011.d1 | EST | 75.00 (gi 2500006) |
| wr1.pk0075.c11 | EST | 5.70 (gi 2984098) |

The data in Table 6 represents a calculation of the percent identity of the amino acid sequences set forth in SEQ ID NOs:4, 6 and 8 and the *Aquifex aeeolicus* and *Corynebacterium sp.* sequences.

TABLE 6

Percent Identity of Amino Acid Sequences Deduced From the Nucleotide Sequences of cDNA Clones Encoding Polypeptides Homologous to *Aquifex aeeolicus* and Corynebacterium sp. Formyltetrahydrofolate Deformylase

| SEQ ID NO. | Percent Identity to |
| --- | --- |
| 4 | 46% (gi 2984098) |
| 6 | 49% (gi 250006) |
| 8 | 30% (gi 2984098) |

Sequence alignments and percent identity calculations were performed using the MEGALIGN™ program of the LASERGENE® bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a formyltetrahydrofolate deformylase. These sequences represent the first corn, rice and wheat sequences encoding formyltetrahydrofolate deformylase.

EXAMPLE 5

Characterization of cDNA Clones Encoding Glutamate Formiminotransferase

The BLASTX search using the EST sequences from clones listed in Table 7 revealed similarity of the polypeptides encoded by the cDNAs to glutamate formiminotransferase from *Aquifex aeeolicus* (NCBI Identifier No. gi 1706872). Shown in Table 7 are the BLAST results for individual ESTs ("EST"), the sequences of the entire cDNA inserts comprising the indicated cDNA clones ("FIS"), or contigs assembled from two or more ESTs ("Contig"):

TABLE 7

BLAST Results for Sequences Encoding Polypeptides Homologous to *Aquifex aeeolicus* Glutamate Formiminotransferase

| Clone | Status | BLAST pLog Score to (gi 1706872) |
| --- | --- | --- |
| r1s6.pk0086.g2 | EST | 12.05 |
| sf11.pk003.o10 | EST | 7.00 |
| wre1n.pk0041.e8 | EST | 13.30 |

The data in Table * represents a calculation of the percent identity of the amino acid sequences set forth in SEQ ID NOs: 10, 12 and 14 and the *Aquifex aeeolicus* sequence.

TABLE 8

Percent Identity of Amino Acid Sequences Deduced From the Nucleotide Sequences of cDNA Clones Encoding Polypeptides Homologous to *Aquifex aeeolicus* Glutamate Formiminotransferase

| SEQ ID NO. | Percent Identity to (gi 1706872) |
| --- | --- |
| 10 | 20% |
| 12 | 24% |
| 14 | 20% |

Sequence alignments and percent Identity calculations were performed using the MEGALIGN™ program of the LASERGENE® bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a glutamate formiminotransferase. These sequences represent the first rice, soybean and wheat sequences encoding glutamate formiminotransferase.

EXAMPLE 6

Characterization of cDNA Clones Encoding Methylenetetrahydrofolate Dehydrogenase The BLASTX search using the EST sequences from clones listed in Table 9 revealed similarity of the polypeptides encoded by the cDNAs to methylenetetrahydrofolate dehydrogenase from *Pisum sativum* (NCBI Identifier No. gi 4103987). Shown in Table 9 are the BLAST results for individual ESTs ("EST"), the sequences of the entire cDNA inserts comprising the indicated cDNA clones ("FIS"), or contigs assembled from two or more ESTs ("Contig"):

TABLE 9

BLAST Results for Sequences Encoding Polypeptides Homologous to *Pisum sativum* Methylenetetrahydrofolate Dehydrogenase

| Clone | Status | BLAST pLog Score to (gi 4103987) |
| --- | --- | --- |
| Contig composed of:<br>cbn10.pk0021.f6<br>cbn2.pk0047.b3<br>cbn2n.pk0012.g11<br>cc71.pk0002.f2<br>cco1n.pk0041.d9<br>cen3n.pk0027.c12<br>cen3n.pk0128.d9<br>cr1n.pk0196.f11<br>cta1n.pk0073 g9 | Contig | 130.00 |
| r1r6.pk0059.b1 | EST | 113.00 |
| ses2w.pk0009.d8 | EST | 88.70 |
| Contig composed of:<br>wdk1c.pk012.f19<br>w11.pk0006.h11<br>w1e1n.pk0031.g8<br>wr1.pk0101.c9<br>wr1.pk0118.c6<br>wre1n.pk170.f4<br>wre1n.pk170.g10 | Contig | 82.15 |

The data in Table 10 represents a calculation of the percent identity of the amino acid sequences set forth in SEQ ID NOs: 16, 18 and 20 and the *Pisum sativum* sequence.

TABLE 10

Percent Identity of Amino Acid Sequences Deduced From the Nucleotide Sequences of cDNA Clones Encoding Polypeptides Homologous to *Pisum sativum* Methylenetetrahydrofolate Dehydrogenase

| SEQ ID NO. | Percent Identity to (gi 4103987) |
| --- | --- |
| 16 | 78% |
| 18 | 66% |
| 20 | 63% |
| 22 | 55% |

Sequence alignments and percent identity calculations were performed using the MEGALIGN™ program of the LASERGENE® bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a methylenetetrahydrofolate dehydrogenase. These sequences represent the first corn, rice and soybean sequences encoding methylenetetrahydrofolate dehydrogenase.

EXAMPLE 7

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SamI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XLI BLUE® (EPICURIAN COLI® XL-1 BLUE®; Stratagene). Bacterial transformants can be screened by restriction enzyme digestion of plasmid DNA and limited nucleotide sequence analysis using the dideoxy chain termination method (SEQUENASE®DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) Nature 627:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a KAPTON®flying disc (Bio-Rad Labs). The particles are then accelerated into the corn tissue with a BIOLISTIC® PDS-1000/He Particle Delivery System (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

EXAMPLE 8

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DUPONT® BIOLISTIC® PDS1000/HE Particle Delivery System instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60 ×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 9

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NUSIEVE® GTG® low melting point agarose gel (FMC). Buffer and agarose contain 10 µg/ml ethidium bromide for visualization of the DNA fragment. The fragment can then be purified from the agarose gel by digestion with GELASE™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5® electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

EXAMPLE 10

Evaluating Compounds for Their Ability to Inhibit the Activity of Tetrahydrofolate Metabolism Enzymes The polypeptides described herein may be produced using any number of methods known to those skilled in the art. Such methods include, but are not limited to, expression in bacteria as described in Example 9, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as SEPHAROSE® 4B resin. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the THIOBOND™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity.

SEQUENCE LISTING

<160> NUMBER OF SEQ ID NOS: 22

<210> SEQ ID NO 1
<211> LENGTH: 560
<212> TYPE: DNA
<213> ORGANISM: Zea mays
<220> FEATURE:
<221> NAME/KEY: unsure
<222> LOCATION: (442)
<221> NAME/KEY: unsure
<222> LOCATION: (520)

<400> SEQUENCE: 1

```
gctccccaca ggcccacacc aaccaactct ctctgcctcg gtccctccgc ccgtacgcgc    60
gacgagagac acgatgcggc ggtccctccc cctcctcctc gcgcggcagg tggcgcggca   120
gcggcggctg agcaacgtgc cggagtccac cgtctacggg ggcccacgcc cgcaggagtc   180
ctcggcggcg cggcgcgtga cggtgaccac actccgtggg aagcaccgcc gcggggagcc   240
catcaccgtc gtcaccgcct acgactaccc ctcggcggtc cacgtcgact ccgccggcat   300
cgacgtctgc ctcgtcgggg actccgccgc catggtcgtc cacggccacg acaccacgct   360
ccccatcacg ctcgacatca tgctcgaagc actgccgcgc cgttggcccg gggcgcgccg   420
cgcccgctcc tcgtcgggga tntccaattc ggctgctaca atccttcggc gccaagctgt   480
tgattaaccg ttaaggtctc aaggaagtgg atggtgcatn aactggaagg ggtgccatca   540
ggttattgaa caaaggtatt                                               560
```

<210> SEQ ID NO 2
<211> LENGTH: 375
<212> TYPE: PRT
<213> ORGANISM: Zea mays

<400> SEQUENCE: 2

```
Pro Thr Gly Pro His Gln Pro Thr Leu Ser Ala Ser Val Pro Pro Pro
  1               5                  10                  15

Val Arg Ala Thr Arg Asp Thr Met Arg Arg Ser Leu Pro Leu Leu Leu
             20                  25                  30

Ala Arg Gln Val Ala Arg Gln Arg Leu Ser Asn Val Pro Glu Ser
         35                  40                  45

Thr Val Tyr Gly Gly Pro Arg Pro Gln Glu Ser Ala Ala Arg Arg
     50                  55                  60

Val Thr Val Thr Thr Leu Arg Gly Lys His Arg Arg Gly Glu Pro Ile
 65                  70                  75                  80

Thr Val Val Thr Ala Tyr Asp Tyr Pro Ser Ala Val His Val Asp Ser
                 85                  90                  95

Ala Gly Ile Asp Val Cys Leu Val Gly Asp Ser Ala Ala Met Val Val
            100                 105                 110

His Gly His Asp Thr Thr Leu Pro Ile Thr Leu Asp Ile Met Leu Glu
        115                 120                 125

His Cys Arg Ala Val Ala Arg Gly Ala Pro Arg Pro Leu Leu Val Gly
    130                 135                 140

Asp Leu Pro Phe Gly Cys Tyr Glu Ser Ser Ala Ala Gln Ala Val Asp
145                 150                 155                 160

Ser Ala Val Arg Val Leu Lys Glu Gly Gly Met Asp Ala Ile Lys Leu
                165                 170                 175

Glu Gly Gly Ala Pro Ser Arg Ile Thr Ala Ala Lys Ala Ile Val Glu
```

```
                        180                 185                 190
Ala Gly Ile Ala Val Met Gly His Val Gly Leu Thr Pro Gln Ala Ile
            195                 200                 205

Ser Val Leu Gly Gly Phe Arg Pro Gln Gly Lys Thr Val Asp Ser Ala
    210                 215                 220

Ile Lys Val Val Glu Thr Ala Leu Ala Leu Gln Glu Ala Gly Cys Phe
225                 230                 235                 240

Ser Val Val Leu Glu Cys Val Pro Ala Pro Val Ala Ala Ala Thr
                245                 250                 255

Ser Ala Leu Lys Ile Pro Thr Ile Gly Ile Gly Ala Gly Pro Phe Cys
                260                 265                 270

Ser Gly Gln Val Leu Val Tyr His Asp Leu Leu Gly Met Leu Gln His
    275                 280                 285

Pro His His Ala Lys Val Thr Pro Lys Phe Cys Lys Gln Phe Gly Asn
    290                 295                 300

Val Gly Asp Val Ile Asn Lys Ala Leu Ser Glu Tyr Lys Gln Glu Val
305                 310                 315                 320

Glu Ala Gln Ala Phe Pro Gly Pro Ser His Thr Pro Tyr Lys Ile Thr
                325                 330                 335

Pro Thr Asp Val Asp Gly Phe Ala Asp Ala Leu Gln Lys Met Gly Leu
                340                 345                 350

Ser Asp Ala Ala Asp Ala Ala Ala Ala Ala Glu Asn Arg Glu Lys
            355                 360                 365

Gly Gly Glu Pro Asn Gly Glu
    370                 375

<210> SEQ ID NO 3
<211> LENGTH: 652
<212> TYPE: DNA
<213> ORGANISM: Zea mays
<220> FEATURE:
<221> NAME/KEY: unsure
<222> LOCATION: (595)

<400> SEQUENCE: 3
gctctataga tggcaagaag gcaggcttcc agtacacatt aattgtgtca ttagcaacca      60
tgatagacca cagataatca tgtacggcgt tttctccaga ggcatggaat cccataccac    120
tacttaccca ccgcacctgc caacaaaaga gagaaagaga tcttggaatt gatccagggt    180
acagattttg ttgtgctggc aagatacatg cagatactct cagaaaacct gttaaaagca    240
tatggtaaag acattatcaa tattcatcat ggccttcttc cctcatttaa gggagggaat    300
ccttcaagac aggccttcag tgctggggtg aagttaatcg gggcaactag ccatttcgtt    360
actccagaac ttgatgctgg gccaatcatt gaacagatgg ttgaacgagt ctctcaccga    420
gacacgttac agagttttgt tgtcaagtct gagaaccttg agaagcagtg cttaacagaa    480
gctatcaagt catattgcga gcttcgtgtc taccatatga actcaggaag actgtcgtgg    540
tctgatctga gcttccttta ttttctggct taattggact tttatatggg attgntaaaa    600
tgaaattttt aactttaaat atattcattc ccctcgacaa ttattttaag gg            652

<210> SEQ ID NO 4
<211> LENGTH: 169
<212> TYPE: PRT
<213> ORGANISM: Zea mays

<400> SEQUENCE: 4
```

```
Leu Tyr Arg Trp Gln Glu Gly Arg Leu Pro Val His Ile Asn Cys Val
 1               5                  10                  15

Ile Ser Asn His Asp Arg Val Arg Arg Phe Leu Gln Arg His Gly Ile
            20                  25                  30

Pro Tyr His Tyr Leu Pro Thr Ala Pro Ala Asn Lys Arg Glu Lys Glu
        35                  40                  45

Ile Leu Glu Leu Ile Gln Gly Thr Asp Phe Val Leu Ala Arg Tyr
 50                  55                  60

Met Gln Ile Leu Ser Glu Asn Leu Leu Lys Ala Tyr Gly Lys Asp Ile
 65                  70                  75                  80

Ile Asn Ile His His Gly Leu Leu Pro Ser Phe Lys Gly Asn Pro
                85                  90                  95

Ser Arg Gln Ala Phe Ser Ala Gly Val Lys Leu Ile Gly Ala Thr Ser
            100                 105                 110

His Phe Val Thr Pro Glu Leu Asp Ala Gly Pro Ile Ile Glu Gln Met
            115                 120                 125

Val Glu Arg Val Ser His Arg Asp Thr Leu Gln Ser Phe Val Val Lys
 130                 135                 140

Ser Glu Asn Leu Glu Lys Gln Cys Leu Thr Glu Ala Ile Lys Ser Tyr
145                 150                 155                 160

Cys Glu Leu Arg Val Tyr His Met Asn
                165

<210> SEQ ID NO 5
<211> LENGTH: 563
<212> TYPE: DNA
<213> ORGANISM: Oryza sativa
<220> FEATURE:
<221> NAME/KEY: unsure
<222> LOCATION: (505)
<221> NAME/KEY: unsure
<222> LOCATION: (510)
<221> NAME/KEY: unsure
<222> LOCATION: (545)

<400> SEQUENCE: 5
tacagcgcca tcagttcaac ctgacaatcg gcgaagaaac tcaattgccg tccccaccaa      60
ttctgaaagt ccaccacttt cggcccaccc ccctccaacc ccaaattcaa caatcatggc    120
cgccaacgac gaccacatcc tgacgctgtc atgcccggac aagccgggca tcgtccacgc    180
cgtgactggc atctttgcct cgcggtcggt caacattctt gacctgaagc agttctccga    240
cacggggtcg caaaagttct tcatgcgggt gcactttggc ccagtggccg agacggcgga    300
cctctctgcc gacttctcgg ctctggcgtc gcagtacgac cccatgacct gggacatccg    360
gcccgtggcg caaaagacgc gcgtcctgat atggtgtcaa gatcggcact gtctcaacga    420
cctgctgttc cgcgcccaga gcggccgcct cgccgtcact ggcctcatcg tgtcaacacc    480
cgacttgcgc cctggcgcag cacgngtcan tcgcactgcc gtcacaagaa caagaccaca    540
ggagnagaat ccaactgcaa gac                                           563

<210> SEQ ID NO 6
<211> LENGTH: 278
<212> TYPE: PRT
<213> ORGANISM: Oryza sativa

<400> SEQUENCE: 6

His Ile Leu Thr Leu Ser Cys Pro Asp Lys Pro Gly Ile Val His Ala
 1               5                  10                  15
```

-continued

```
Val Thr Gly Ile Phe Ala Ser Arg Ser Val Asn Ile Leu Asp Leu Lys
                20                  25                  30

Gln Phe Ser Asp Thr Gly Ser Gln Lys Phe Phe Met Arg Val His Phe
         35                  40                  45

Gly Pro Val Ala Glu Thr Ala Asp Leu Ser Ala Asp Phe Ser Ala Leu
     50                  55                  60

Ala Ser Gln Tyr Asp Pro Met Thr Trp Asp Ile Arg Pro Val Ala Gln
 65                  70                  75                  80

Lys Thr Arg Val Leu Ile Met Val Ser Lys Ile Gly His Cys Leu Asn
                 85                  90                  95

Asp Leu Leu Phe Arg Ala Gln Ser Gly Arg Leu Ala Val Asp Val Ala
            100                 105                 110

Leu Ile Val Ser Asn His Pro Asp Phe Ala Pro Leu Ala Ala Ser His
        115                 120                 125

Gly Val Glu Phe Arg His Leu Pro Val Thr Lys Glu Thr Lys Thr Gln
    130                 135                 140

Gln Glu Glu Glu Ile Leu Lys Leu Ala Lys Glu Arg Asp Val Glu Leu
145                 150                 155                 160

Ile Val Leu Ala Arg Tyr Met Gln Val Leu Ser Pro Thr Leu Cys Glu
                165                 170                 175

Ala Met Ser Gly Arg Ile Ile Asn Ile His His Ser Phe Leu Pro Ser
            180                 185                 190

Phe Lys Gly Ala Lys Pro Tyr His Gln Ala Tyr Asp Arg Gly Val Lys
        195                 200                 205

Ile Ile Gly Ala Thr Ala His Phe Val Thr Ala Asp Leu Asp Glu Gly
    210                 215                 220

Pro Ile Ile Glu Gln Arg Ile Ser Arg Val Asp His Gly Met Thr Pro
225                 230                 235                 240

Lys Gln Leu Val Asp Glu Gly Ser Ser Ile Glu Ala Leu Val Leu Gly
                245                 250                 255

Ala Ala Val Gln Trp Phe Ala Glu Arg Arg Val Phe Leu Asn Asn Ser
            260                 265                 270

Lys Thr Val Val Phe Asn
        275
```

<210> SEQ ID NO 7
<211> LENGTH: 594
<212> TYPE: DNA
<213> ORGANISM: Triticum aestivum
<220> FEATURE:
<221> NAME/KEY: unsure
<222> LOCATION: (358)
<221> NAME/KEY: unsure
<222> LOCATION: (374)
<221> NAME/KEY: unsure
<222> LOCATION: (383)
<221> NAME/KEY: unsure
<222> LOCATION: (439)
<221> NAME/KEY: unsure
<222> LOCATION: (443)
<221> NAME/KEY: unsure
<222> LOCATION: (461)
<221> NAME/KEY: unsure
<222> LOCATION: (478)
<221> NAME/KEY: unsure
<222> LOCATION: (494)
<221> NAME/KEY: unsure
<222> LOCATION: (509)
<221> NAME/KEY: unsure
<222> LOCATION: (526)
<221> NAME/KEY: unsure
<222> LOCATION: (536)

<221> NAME/KEY: unsure
<222> LOCATION: (547)
<221> NAME/KEY: unsure
<222> LOCATION: (558)
<221> NAME/KEY: unsure
<222> LOCATION: (565)
<221> NAME/KEY: unsure
<222> LOCATION: (567)
<221> NAME/KEY: unsure
<222> LOCATION: (578)
<221> NAME/KEY: unsure
<222> LOCATION: (593)..(594)

<400> SEQUENCE: 7

```
caacccgagg ctatggccgc gcgacgtgct tcgcgccgac ttcctccgcc tgtcggactg    60
cttcagcgcg caaaaatcca ctgtgcgagt acctgacatc gaccccaagt acaagattgc   120
agtcctcgct tcgaagcagg accattgtct gtttgacttg ctgcatagat ggcaagaagg   180
caggcttcca gttgacattc attgtgtgat aagcaaccat gatcgacctg tagataacca   240
tgtgatgcgt tttcttcaag aggcacgaaa tcccctatca ttacttacca acgacttcct   300
gggaataaaa gggaacaaga gatattagaa ttgattgaag atacagattt tgttgtgntg   360
ggcaagatat gcangtaatg tcngaaactt ccttaaacat atgggaaaga tattattata   420
tcacaaggct ccttcctcng tcaaaggag gatcctctag naggctcaat gctgggtnaa    480
ttgattggtg cacnaccatt tgtacccana cttagcgggc aacatngacc aaggtnaacg   540
gtcccanagg aaattaaanac ttgtntnatc tgaaactngg aacatccaca aann         594
```

<210> SEQ ID NO 8
<211> LENGTH: 70
<212> TYPE: PRT
<213> ORGANISM: Triticum aestivum

<400> SEQUENCE: 8

```
Pro Arg Asp Val Leu Arg Ala Asp Phe Leu Arg Leu Ser Asp Cys Phe
  1               5                  10                  15

Ser Ala Gln Lys Ser Thr Val Arg Val Pro Asp Ile Asp Pro Lys Tyr
             20                  25                  30

Lys Ile Ala Val Leu Ala Ser Lys Gln Asp His Cys Leu Phe Asp Leu
         35                  40                  45

Leu His Arg Trp Gln Glu Gly Arg Leu Pro Val Asp Ile His Cys Val
     50                  55                  60

Ile Ser Asn His Asp Arg
 65                  70
```

<210> SEQ ID NO 9
<211> LENGTH: 543
<212> TYPE: DNA
<213> ORGANISM: Oryza sativa
<220> FEATURE:
<221> NAME/KEY: unsure
<222> LOCATION: (381)
<221> NAME/KEY: unsure
<222> LOCATION: (440)
<221> NAME/KEY: unsure
<222> LOCATION: (449)
<221> NAME/KEY: unsure
<222> LOCATION: (466)
<221> NAME/KEY: unsure
<222> LOCATION: (470)
<221> NAME/KEY: unsure
<222> LOCATION: (507)
<221> NAME/KEY: unsure
<222> LOCATION: (521)
<221> NAME/KEY: unsure

<222> LOCATION: (524)

<400> SEQUENCE: 9

```
gttctaacgc tgcaagctct acatttctga aagccagaat gccaaggttg ttgatgcaat      60
cactcgcatt ggccagaaag accctgaggt tgttttgctc agcaagttcg aagatgacca     120
ctacaaccgt gtccgttaca cgcttgcgtc ttatatcatc aacgagaact caactggtga     180
agtgaaattt agcccaatga ggcgagtatt gttggagatg attgagaaag cgttttcaac     240
cataaacctt gaaacgcaca ctgggaactc acccaaggat tggagtcatt gatgacatgt     300
ccttccaccc cttgaatcaa gccacaatgg aagatgctgc tcaactggct aagactgtgg     360
cctctgacat tggcaacttc ntacaagtcc cagtatcctg tatggagcag cacaccccac     420
tggcaaacct gtgactgcan acggcgtna actgggctac ttccanccan attcatggc      480
atccaatggg atgggtcagg tacccntga tatctgcggg naaccagat aagggccagt     540
ttg                                                                    543
```

<210> SEQ ID NO 10
<211> LENGTH: 296
<212> TYPE: PRT
<213> ORGANISM: Oryza sativa

<400> SEQUENCE: 10

```
Arg Cys Lys Leu Tyr Ile Ser Glu Ser Gln Asn Ala Lys Val Val Asp
  1               5                  10                  15

Ala Ile Thr Arg Ile Gly Gln Lys Asp Pro Glu Val Val Leu Leu Ser
             20                  25                  30

Lys Phe Glu Asp Asp His Tyr Asn Arg Val Arg Tyr Thr Leu Ala Ser
         35                  40                  45

Tyr Ile Ile Asn Glu Asn Ser Thr Gly Glu Val Lys Phe Ser Pro Met
     50                  55                  60

Arg Arg Val Leu Leu Glu Met Ile Glu Lys Ala Phe Ser Thr Ile Asn
 65                  70                  75                  80

Leu Glu Thr His Thr Gly Thr His Pro Arg Ile Gly Val Ile Asp Asp
                 85                  90                  95

Met Ser Phe His Pro Leu Asn Gln Ala Thr Met Glu Asp Ala Ala Gln
            100                 105                 110

Leu Ala Lys Thr Val Ala Ser Asp Ile Gly Asn Phe Leu Gln Val Pro
        115                 120                 125

Val Phe Leu Tyr Gly Ala Ala His Pro Thr Gly Lys Pro Val Thr Ala
    130                 135                 140

Val Arg Arg Glu Leu Gly Tyr Phe Gln Pro Asn Tyr Met Gly Ile Gln
145                 150                 155                 160

Trp Met Gly Gln Val Leu Pro Asp Ile Leu Pro Val Lys Pro Asp Glu
                165                 170                 175

Gly Pro Asp His Val Ser Arg Glu Arg Gly Ala Ile Met Ile Gly Ala
            180                 185                 190

Ala Pro Leu Pro Leu Asn Tyr Asn Val Pro Val Leu Ser Lys Asp Ile
        195                 200                 205

Pro Thr Ile Arg Arg Ile Thr Arg Arg Val Thr Gly Arg Gly Gly
    210                 215                 220

Leu Pro Thr Val Gln Ala Leu Ala Leu Ser His Gly Asp Asp Cys Thr
225                 230                 235                 240

Glu Ile Ala Cys Phe Leu Asp Pro Asp His Val Ser Ala Asp Gln Val
                245                 250                 255
```

```
Gln Gln Gln Val Glu Gln Ile Ala Ala Glu Gln Gly Leu Glu Val Glu
            260                 265                 270

Lys Gly Tyr Phe Thr Asp Phe Ser Lys Asp Ala Met Leu Glu Lys Tyr
        275                 280                 285

Phe Lys Ile Val Leu Ser Val Asp
    290                 295

<210> SEQ ID NO 11
<211> LENGTH: 468
<212> TYPE: DNA
<213> ORGANISM: Glycine max
<220> FEATURE:
<221> NAME/KEY: unsure
<222> LOCATION: (398)
<221> NAME/KEY: unsure
<222> LOCATION: (423)
<221> NAME/KEY: unsure
<222> LOCATION: (446)
<221> NAME/KEY: unsure
<222> LOCATION: (467)

<400> SEQUENCE: 11
ggaaatccca tatacagccc cttgcaccaa actgtcatag ccatggctga ggctacattc      60
aatgccatca acctcgaatt ccatgaaggt gctcaccctc gcttgggcgc actcgacgac     120
attatcttcc atccacttgg tcatgcgtcg ctcgacgagg cagcttggct tgccaaagca     180
gtggcagcag acattggcaa ccgattcagt gtgccagtgt ttctgtacgc cgcagcccac     240
ccaacaggga aggaaagttg atgccataag gcgagagctc ggatattacc ggccaaattc     300
aaggggaagt caatgggccg ggtgggcaat gcccgaaacg ctaccgctga gcctgatgaa     360
gggccaaacg tgggtttcaa gagctaaagg catcacantt gattgggtgc acgcccttg     420 ggnttacatt ctacaacgtt ccaatncctt tgcactgatg tgtcaant                  468

<210> SEQ ID NO 12
<211> LENGTH: 128
<212> TYPE: PRT
<213> ORGANISM: Glycine max
<220> FEATURE:
<221> NAME/KEY: UNSURE
<222> LOCATION: (87)

<400> SEQUENCE: 12

Gly Asn Pro Ile Tyr Ser Pro Leu His Gln Thr Val Ile Ala Met Ala
  1               5                  10                  15

Glu Ala Thr Phe Asn Ala Ile Asn Leu Glu Phe His Glu Gly Ala His
             20                  25                  30

Pro Arg Leu Gly Ala Leu Asp Asp Ile Ile Phe His Pro Leu Gly His
         35                  40                  45

Ala Ser Leu Asp Glu Ala Ala Trp Leu Ala Lys Ala Val Ala Ala Asp
     50                  55                  60

Ile Gly Asn Arg Phe Ser Val Pro Val Phe Leu Tyr Ala Ala Ala His
 65                  70                  75                  80

Pro Thr Gly Lys Glu Ser Xaa Cys His Lys Ala Arg Ala Arg Ile Leu
                 85                  90                  95

Pro Ala Lys Phe Lys Gly Lys Ser Met Gly Arg Val Gly Asn Ala Arg
            100                 105                 110

Asn Ala Thr Ala Glu Pro Asp Glu Gly Pro Asn Val Gly Phe Lys Ser
        115                 120                 125
```

```
<210> SEQ ID NO 13
<211> LENGTH: 416
<212> TYPE: DNA
<213> ORGANISM: Triticum aestivum
<220> FEATURE:
<221> NAME/KEY: unsure
<222> LOCATION: (393)
<221> NAME/KEY: unsure
<222> LOCATION: (398)
<221> NAME/KEY: unsure
<222> LOCATION: (405)

<400> SEQUENCE: 13
tcgaaggtga tctgttgcaa gctctacatc tctgaaagcc aaaatgcggc tgttgtcgat      60
gccatcagcc gcataggcca gaaagaccct gaggtggttc tactcaacaa gttcgaggat     120
gagtactaca accgtgtccg ctacacgctt gtctcctaca tcaccaacga aagctcgact     180
ggtggagctg tatttagccc aatcaggaag gtactgctgg cgatgatcga ggctgcattt     240
tcagccataa acctcgaagt gcactgtgga actcatccaa ggattggtgt cgtcgatgac     300
atttcattcc accccttgaa tcaagcggac acaatagagg atgctgctca gctggtaagc     360
tggtacctct gacattggaa tggttcaatt cantggtncc aaaangcgga acaata         416

<210> SEQ ID NO 14
<211> LENGTH: 302
<212> TYPE: PRT
<213> ORGANISM: Triticum aestivum

<400> SEQUENCE: 14
```

Ser Lys Val Ile Cys Cys Lys Leu Tyr Ile Ser Glu Ser Gln Asn Ala
 1               5                  10                  15

Ala Val Val Asp Ala Ile Ser Arg Ile Gly Gln Lys Asp Pro Glu Val
                20                  25                  30

Val Leu Leu Asn Lys Phe Glu Asp Glu Tyr Tyr Asn Arg Val Arg Tyr
            35                  40                  45

Thr Leu Val Ser Tyr Ile Thr Asn Glu Ser Ser Thr Gly Gly Ala Val
        50                  55                  60

Phe Ser Pro Ile Arg Lys Val Leu Leu Ala Met Ile Glu Ala Ala Phe
 65                  70                  75                  80

Ser Ala Ile Asn Leu Glu Val His Cys Gly Thr His Pro Arg Ile Gly
                85                  90                  95

Val Val Asp Asp Ile Ser Phe His Pro Leu Asn Gln Ala Asp Thr Ile
            100                 105                 110

Glu Asp Ala Ala Gln Leu Ala Lys Leu Val Ala Ser Asp Ile Gly Asn
        115                 120                 125

Gly Leu Gln Val Pro Val Phe Leu Tyr Ala Ala His Pro Thr Ser
    130                 135                 140

Lys Ser Val Ser Ala Val Arg Arg Glu Leu Gly Tyr Phe Arg Pro Asn
145                 150                 155                 160

His Lys Gly Val Gln Trp Ala Gly Pro Val Leu Pro Asp Thr Leu Pro
                165                 170                 175

Met Lys Pro Asp Val Gly Pro Val His Val Pro Arg Glu Arg Gly Ala
            180                 185                 190

Thr Met Val Gly Ala Gln Pro Leu Val Glu Ser Tyr Asn Val Pro Ile
        195                 200                 205

Phe Cys Lys Asp Val Pro Thr Val Arg Arg Ile Thr Arg Val Thr
    210                 215                 220

Gly Arg Ser Gly Gly Leu Pro Ser Val Gln Ala Leu Ala Leu Phe His

```
            225                 230                 235                 240
Gly Asp Asn Cys Thr Glu Ile Ala Cys Phe Leu Leu Asp Pro Asp His
                245                 250                 255

Val Gly Ala Asp Arg Val Gln Trp Leu Val Gln Ile Ala Glu Glu
            260                 265                 270

Gln Gly Leu Glu Val Glu Lys Gly Tyr Phe Thr Asp Leu Ser Lys His
        275                 280                 285

Met Met Leu Glu Arg Tyr Ser Glu Met Val Ser Ala Ala Asp
    290                 295                 300
```

```
<210> SEQ ID NO 15
<211> LENGTH: 1076
<212> TYPE: DNA
<213> ORGANISM: Zea mays

<400> SEQUENCE: 15
gcacgagcca agaaccacag ccaccgcgat ggcgcagatc atcgatggca aggccatcgc      60
cgccgacgtc cgccgcgagg tcgccgccga tgtggccgcg ctctcgtcgg cccacggact     120
cgtgccgggg ctggccgtgg tcatcgtggg gagcaggaag gactcgcaga cgtacgtgaa     180
catgaagcgc aaggcgtgcg ccgaggtcgg catctgctcc atcgacgtcg acctcccgga     240
ggacatctcc gagaccgcgc tcgtcgccga ggttcatcgc ctcaacgctg accccgcagt     300
gcacgggatc cttgtccagc ttccacttcc taagcatatc aacgaagaga agatactgag     360
cgagatttcc atcgagaaag atgtggatgg cttccatcct ctcaacattg caagcttgc      420
aatgaaaggc agagagccac tgttcgtacc atgtacgcca aagggtgca tggagctctt      480
gtcaaggagc ggagtcactg ttaaaggtaa gcgggcagtt gtggttggtc gcagcaacat     540
cgtcgggcta cctgtatccc tgctccttct gaaggcagat gcgaccgtat ctgttgtgca     600
ctcgcggacc cctgatcctg aaagcattgt acgcgaagct gacatagtca tcgcggcagc     660
tgggcaggct atgatgatca aggtgactg atcaagcca ggtgctgcgg tcatcgatgt       720
cgggacgaac tccatcgatg accctaccg gaagtccggg gtacggctcg tcggcgatgt      780
ggatttcgca gcggcgagca aggttgctgg gtacctgact ccggttcccg gaggcgttgg     840
cccaatgacg gtggcaatgc tgctgaagaa cacggtggat ggggcaaagc gggggatagt     900
cgagtagcta cgttcatctc acttcacgtt gctgtacggc ctgtgttgca aggatgtgag     960
ctgactcgaa aagcgtgtgt tggttggtga acaatctgtt tcccaagaat aagaatgata    1020
gtcacagctg ttttcctgtt taataaatgc aatgaagaaa gaattttggc tttaaa        1076
```

```
<210> SEQ ID NO 16
<211> LENGTH: 290
<212> TYPE: PRT
<213> ORGANISM: Zea mays

<400> SEQUENCE: 16

Met Ala Gln Ile Ile Asp Gly Lys Ala Ile Ala Ala Asp Val Arg Arg
  1               5                  10                  15

Glu Val Ala Ala Asp Val Ala Ala Leu Ser Ser Ala His Gly Leu Val
                 20                  25                  30

Pro Gly Leu Ala Val Val Ile Val Gly Ser Arg Lys Asp Ser Gln Thr
            35                  40                  45

Tyr Val Asn Met Lys Arg Lys Ala Cys Ala Glu Val Gly Ile Cys Ser
        50                  55                  60

Ile Asp Val Asp Leu Pro Glu Asp Ile Ser Glu Thr Ala Leu Val Ala
```

```
                65                  70                  75                  80
Glu Val His Arg Leu Asn Ala Asp Pro Ala Val His Gly Ile Leu Val
                        85                  90                  95
Gln Leu Pro Leu Pro Lys His Ile Asn Glu Glu Lys Ile Leu Ser Glu
                100                 105                 110
Ile Ser Ile Glu Lys Asp Val Asp Gly Phe His Pro Leu Asn Ile Gly
            115                 120                 125
Lys Leu Ala Met Lys Gly Arg Glu Pro Leu Phe Val Pro Cys Thr Pro
    130                 135                 140
Lys Gly Cys Met Glu Leu Leu Ser Arg Ser Gly Val Thr Val Lys Gly
145                 150                 155                 160
Lys Arg Ala Val Val Gly Arg Ser Asn Ile Val Gly Leu Pro Val
                165                 170                 175
Ser Leu Leu Leu Lys Ala Asp Ala Thr Val Ser Val Val His Ser
            180                 185                 190
Arg Thr Pro Asp Pro Glu Ser Ile Val Arg Glu Ala Asp Ile Val Ile
        195                 200                 205
Ala Ala Ala Gly Gln Ala Met Met Ile Lys Gly Asp Trp Ile Lys Pro
    210                 215                 220
Gly Ala Ala Val Ile Asp Val Gly Thr Asn Ser Ile Asp Asp Pro Thr
225                 230                 235                 240
Arg Lys Ser Gly Val Arg Leu Val Gly Asp Val Asp Phe Ala Ala Ala
                245                 250                 255
Ser Lys Val Ala Gly Tyr Leu Thr Pro Val Pro Gly Val Gly Pro
            260                 265                 270
Met Thr Val Ala Met Leu Leu Lys Asn Thr Val Asp Gly Ala Lys Arg
        275                 280                 285
Gly Ile
    290

<210> SEQ ID NO 17
<211> LENGTH: 579
<212> TYPE: DNA
<213> ORGANISM: Oryza sativa
<220> FEATURE:
<221> NAME/KEY: unsure
<222> LOCATION: (316)
<221> NAME/KEY: unsure
<222> LOCATION: (411)
<221> NAME/KEY: unsure
<222> LOCATION: (490)
<221> NAME/KEY: unsure
<222> LOCATION: (503)
<221> NAME/KEY: unsure
<222> LOCATION: (521)
<221> NAME/KEY: unsure
<222> LOCATION: (548)
<221> NAME/KEY: unsure
<222> LOCATION: (562)

<400> SEQUENCE: 17
gtttaaacgc ggcggcggcg gcgcctcctc taccgactca gatgcttgtg ccaagatcat      60
tgatgggaag ttggtggcaa agcagataag agaggaaatc gctgttgaga tcgccaagat     120
gaaggatgca attggggttg tgcctgggct ggcagtcatc ctagttgggt caaggaagga     180
ttctcaaacg tatgtgcgca acaagaagaa ggcatgcgaa gcggttggta tcaagtcata     240
tgaggttaat ttgccggaag acagctctga ggatgaggtt ctcaagcaca tcgcaacatt     300
taacagtgat ccgtcngtgc atggcatctt ggtcagttcc cctacctcat catatgaatg     360
```

```
atgagaacat tttgaatgct gtagtattga gaaggatgtt gatggattca ncactgaaca      420
ttggcgactg catgcaagcc ggatcgtcct tgtccagcac cctaagatca tggatacacc      480
agatatggan tgaatcaagg aanaactttg tattggcggg nattttggga tctgcgctat      540
acgcaaanca ccacgtacat gnatcaatca gaaccggga                             579
```

```
<210> SEQ ID NO 18
<211> LENGTH: 292
<212> TYPE: PRT
<213> ORGANISM: Oryza sativa

<400> SEQUENCE: 18
```

| Ala | Lys | Ile | Ile | Asp | Gly | Lys | Leu | Val | Ala | Lys | Gln | Ile | Arg | Glu | Glu |
|---|---|---|---|---|---|---|---|---|---|---|---|---|---|---|---|
| 1 | | | | 5 | | | | | 10 | | | | | 15 | |
| Ile | Ala | Val | Glu | Ile | Ala | Lys | Met | Lys | Asp | Ala | Ile | Gly | Val | Val | Pro |
| | | | 20 | | | | | 25 | | | | | 30 | | |
| Gly | Leu | Ala | Val | Ile | Leu | Val | Gly | Ser | Arg | Lys | Asp | Ser | Gln | Thr | Tyr |
| | | 35 | | | | | 40 | | | | | 45 | | | |
| Val | Arg | Asn | Lys | Lys | Ala | Cys | Glu | Ala | Val | Gly | Ile | Lys | Ser | Tyr |
| 50 | | | | | 55 | | | | | 60 | | | | |
| Glu | Val | Asn | Leu | Pro | Glu | Asp | Ser | Ser | Glu | Asp | Glu | Val | Leu | Lys | His |
| 65 | | | | 70 | | | | | 75 | | | | | 80 | |
| Ile | Ala | Thr | Phe | Asn | Ser | Asp | Pro | Ser | Val | His | Gly | Ile | Leu | Val | Gln |
| | | | | 85 | | | | | 90 | | | | | 95 | |
| Leu | Pro | Leu | Pro | His | His | Met | Asn | Asp | Glu | Asn | Ile | Leu | Asn | Ala | Val |
| | | | 100 | | | | | 105 | | | | | 110 | | |
| Ser | Ile | Glu | Lys | Asp | Val | Asp | Gly | Phe | His | Pro | Leu | Asn | Ile | Gly | Arg |
| | | | 115 | | | | | 120 | | | | | 125 | | |
| Leu | Ala | Met | Gln | Gly | Arg | Asp | Pro | Phe | Phe | Val | Pro | Cys | Thr | Pro | Lys |
| 130 | | | | | 135 | | | | | 140 | | | | | |
| Gly | Cys | Met | Glu | Leu | Leu | His | Arg | Tyr | Gly | Val | Glu | Ile | Lys | Gly | Lys |
| 145 | | | | | 150 | | | | | 155 | | | | | 160 |
| Arg | Ala | Val | Val | Ile | Gly | Arg | Ser | Asn | Ile | Val | Gly | Met | Pro | Ala | Ala |
| | | | | 165 | | | | | 170 | | | | | 175 | |
| Leu | Leu | Leu | Gln | Lys | Ala | Asn | Ala | Thr | Val | Ser | Ile | Val | His | Ser | Asn |
| | | | 180 | | | | | 185 | | | | | 190 | | |
| Thr | Lys | Lys | Pro | Glu | Glu | Ile | Thr | Arg | Gln | Ala | Asp | Ile | Val | Ile | Ala |
| | | 195 | | | | | 200 | | | | | 205 | | | |
| Ala | Val | Gly | Val | Ala | Asn | Leu | Val | Arg | Gly | Ser | Trp | Ile | Lys | Pro | Gly |
| | 210 | | | | | 215 | | | | | 220 | | | | |
| Ala | Ala | Ile | Ile | Asp | Val | Gly | Ile | Asn | Pro | Val | Asp | Pro | Glu | Ser |
| 225 | | | | | 230 | | | | | 235 | | | | | 240 |
| Pro | Arg | Gly | Tyr | Arg | Leu | Val | Gly | Asp | Val | Cys | Tyr | Glu | Glu | Ala | Ser |
| | | | | 245 | | | | | 250 | | | | | 255 | |
| Lys | Ile | Ala | Gly | Leu | Ile | Thr | Pro | Val | Pro | Gly | Gly | Val | Gly | Pro | Met |
| | | | 260 | | | | | 265 | | | | | 270 | | |
| Thr | Ile | Ala | Met | Leu | Leu | Ser | Asn | Thr | Leu | Glu | Ser | Ala | Lys | Arg | Ile |
| | | 275 | | | | | 280 | | | | | 285 | | | |
| His | Lys | Phe | Lys |
| | 290 | | |

```
<210> SEQ ID NO 19
<211> LENGTH: 926
<212> TYPE: DNA
<213> ORGANISM: Glycine max
```

<400> SEQUENCE: 19

```
gcagagagaa gaaggcttgt gaatctgttg gaatcaattc tttggaagca atctgcctg      60
agaattccac agaagaagaa gttttgaact atattgcagg ctacaatgat gatccttcag    120
ttcatggcat cctcgttcag ttaccttac cttcgcatat gaatgagcag aacatcttga    180
acgctgtcag gattgagaag gatgtagatg gttttcatcc gttaaatatt ggtcgtcttg    240
ccatgcgtgg aagagaacct ctgtttgttc cttgtacacc aaagggatgc atagagctac    300
tgcacagata caatgtttct attaaaggaa agagggctgt tgtgattggt cggagcaata    360
ttgttggaat gccagctgct ctcttgcttc aaagggaaga tgctactgtc agtattgtcc    420
attctagaac cagtaacccc gaagagatca taagacaggc agatattatc attgctgctg    480
ttgggcaagc aaacatggtg aggggaagct ggataaagcc tggtgcagtc attattgatg    540
ttggaatcaa cccggtagag gatccaaata gcccccgagg ttacaaactg gtgggagatg    600
tttgttatga agaagccata gaattgcct ctgctgttac accagttcct ggaggagttg     660
gtccaatgac catagcaatg cttctacaaa atacactcat ctctgcaaag agggtgcaca    720
attttgaata acattgtgaa agggtgttgt ataccattat gagccatcaa tttttgttta    780
ggtgactcgt ggatttaagg tagggttttt tcaacattgg gacttaagcc ccaaataaga    840
gaaaatgttg ctaaaaaaaa aaaaaaaaa aaaaaaaaaa aaaaaaaca aaaaaaaaa       900
acttgagggg gccccggacc caatat                                         926
```

<210> SEQ ID NO 20
<211> LENGTH: 242
<212> TYPE: PRT
<213> ORGANISM: Glycine max

<400> SEQUENCE: 20

```
Arg Glu Lys Lys Ala Cys Glu Ser Val Gly Ile Asn Ser Leu Glu Ala
  1               5                  10                  15

Asn Leu Pro Glu Asn Ser Thr Glu Glu Val Leu Asn Tyr Ile Ala
             20                  25                  30

Gly Tyr Asn Asp Asp Pro Ser Val His Gly Ile Leu Val Gln Leu Pro
         35                  40                  45

Leu Pro Ser His Met Asn Glu Gln Asn Ile Leu Asn Ala Val Arg Ile
     50                  55                  60

Glu Lys Asp Val Asp Gly Phe His Pro Leu Asn Ile Gly Arg Leu Ala
 65                  70                  75                  80

Met Arg Gly Arg Glu Pro Leu Phe Val Pro Cys Thr Pro Lys Gly Cys
                 85                  90                  95

Ile Glu Leu Leu His Arg Tyr Asn Val Ser Ile Lys Gly Lys Arg Ala
            100                 105                 110

Val Val Ile Gly Arg Ser Asn Ile Val Gly Met Pro Ala Ala Leu Leu
        115                 120                 125

Leu Gln Arg Glu Asp Ala Thr Val Ser Ile Val His Ser Arg Thr Ser
    130                 135                 140

Asn Pro Glu Glu Ile Ile Arg Gln Ala Asp Ile Ile Ala Ala Val
145                 150                 155                 160

Gly Gln Ala Asn Met Val Arg Gly Ser Trp Ile Lys Pro Gly Ala Val
                165                 170                 175

Ile Ile Asp Val Gly Ile Asn Pro Val Glu Asp Pro Asn Ser Pro Arg
            180                 185                 190

Gly Tyr Lys Leu Val Gly Asp Val Cys Tyr Glu Glu Ala Ile Arg Ile
```

```
              195                 200                 205
Ala Ser Ala Val Thr Pro Val Pro Gly Gly Val Gly Pro Met Thr Ile
        210                 215                 220

Ala Met Leu Leu Gln Asn Thr Leu Ile Ser Ala Lys Arg Val His Asn
225                 230                 235                 240

Phe Glu

<210> SEQ ID NO 21
<211> LENGTH: 875
<212> TYPE: DNA
<213> ORGANISM: Triticum aestivum
<220> FEATURE:
<221> NAME/KEY: unsure
<222> LOCATION: (584)
<221> NAME/KEY: unsure
<222> LOCATION: (680)
<221> NAME/KEY: unsure
<222> LOCATION: (699)
<221> NAME/KEY: unsure
<222> LOCATION: (704)
<221> NAME/KEY: unsure
<222> LOCATION: (756)
<221> NAME/KEY: unsure
<222> LOCATION: (767)
<221> NAME/KEY: unsure
<222> LOCATION: (771)
<221> NAME/KEY: unsure
<222> LOCATION: (780)
<221> NAME/KEY: unsure
<222> LOCATION: (800)
<221> NAME/KEY: unsure
<222> LOCATION: (802)
<221> NAME/KEY: unsure
<222> LOCATION: (816)
<221> NAME/KEY: unsure
<222> LOCATION: (834)
<221> NAME/KEY: unsure
<222> LOCATION: (837)
<221> NAME/KEY: unsure
<222> LOCATION: (842)
<221> NAME/KEY: unsure
<222> LOCATION: (846)..(847)
<221> NAME/KEY: unsure
<222> LOCATION: (858)..(859)
<221> NAME/KEY: unsure
<222> LOCATION: (870)
<221> NAME/KEY: unsure
<222> LOCATION: (874)

<400> SEQUENCE: 21
ctctagtgct accccaatgg cgcaaatcat cgacggcaag gccatcgccg ccgaaatcag      60
gcgcgagatc ggcgccgagg tcgccgtgct ctcgtccgcc cacaacatcg tgccggggct     120
ggcggtggtg atcgtgggga gcaggaagga ctcgcagacg tacgtgcaga tgaagcgcaa     180
ggcctgcgcc gaggtcggca tccgctcctt cgacgtcgac ctccccgagg acatcgccga     240
ggccgcgctc gtcgccgagg tccaccgcct caacgccgac cccgccgtcc acggaattct     300
tgttcagctt ccattgccca agcatatcaa cgaagaaaat atcttaaacc agatctccat     360
tgagaaagat gtcgacggct tcatcctttt gaacattggc aagcttgcaa tgaaaggcag     420
agatccactg ttcgtacctt gcacgccaaa gggatgcatg gagctcctgt cacgaagtgg     480
cgtcactgta aaaggaaaac acgcagttgt ggttgggcgt agcaacatcg tgggtttacc     540
aagtatccct tctccttctg aaagcggacg ctaccgtgtc gatngtgcat caacggaccc     600
aaatccccaa acaatttccg tcaagcaaga cattgtcatt gcagcagctg ggcaagccat     660
gatgatcaag ggagactggn ttaaacaaaa gcgcaacgnc atcnacgtcg ggacaatcca     720
```

```
tcgacgacca acaagaatct gggtaaaatc cttggnagtg gttctcngag naacaagccn      780
ggtcactgat cggcccggan gntcggccat actggnattt ctaaaaaagg ggangncaa      840 angganncac gattcgcnna ttgaagggan attna                                 875
```

<210> SEQ ID NO 22
<211> LENGTH: 289
<212> TYPE: PRT
<213> ORGANISM: Triticum aestivum
<220> FEATURE:
<221> NAME/KEY: UNSURE
<222> LOCATION: (195)
<221> NAME/KEY: UNSURE
<222> LOCATION: (227)
<221> NAME/KEY: UNSURE
<222> LOCATION: (233)
<221> NAME/KEY: UNSURE
<222> LOCATION: (235)
<221> NAME/KEY: UNSURE
<222> LOCATION: (252)
<221> NAME/KEY: UNSURE
<222> LOCATION: (256)..(257)
<221> NAME/KEY: UNSURE
<222> LOCATION: (260)
<221> NAME/KEY: UNSURE
<222> LOCATION: (267)
<221> NAME/KEY: UNSURE
<222> LOCATION: (272)
<221> NAME/KEY: UNSURE
<222> LOCATION: (278)..(279)
<221> NAME/KEY: UNSURE
<222> LOCATION: (281)..(282)
<221> NAME/KEY: UNSURE
<222> LOCATION: (286)

<400> SEQUENCE: 22

```
Ser Ser Ala Thr Pro Met Ala Gln Ile Ile Asp Gly Lys Ala Ile Ala
 1               5                  10                  15

Ala Glu Ile Arg Arg Glu Ile Gly Ala Glu Val Ala Val Leu Ser Ser
             20                  25                  30

Ala His Asn Ile Val Pro Gly Leu Ala Val Val Ile Val Gly Ser Arg
         35                  40                  45

Lys Asp Ser Gln Thr Tyr Val Gln Met Lys Arg Lys Ala Cys Ala Glu
     50                  55                  60

Val Gly Ile Arg Ser Phe Asp Val Asp Leu Pro Glu Asp Ile Ala Glu
 65                  70                  75                  80

Ala Ala Leu Val Ala Glu Val His Arg Leu Asn Ala Asp Pro Ala Val
                 85                  90                  95

His Gly Ile Leu Val Gln Leu Pro Leu Pro Lys His Ile Asn Glu Glu
            100                 105                 110

Asn Ile Leu Asn Gln Ile Ser Ile Glu Lys Asp Val Asp Gly Phe His
        115                 120                 125

Pro Leu Asn Ile Gly Lys Leu Ala Met Lys Gly Arg Asp Pro Leu Phe
    130                 135                 140

Val Pro Cys Thr Pro Lys Gly Cys Met Glu Leu Leu Ser Arg Ser Gly
145                 150                 155                 160

Val Thr Val Lys Gly Lys His Ala Val Val Val Gly Arg Ser Asn Ile
                165                 170                 175

Val Gly Leu Pro Ser Ile Pro Ser Pro Ser Glu Ser Gly Arg Tyr Arg
            180                 185                 190

Val Asp Xaa Ala Ser Thr Asp Pro Asn Pro Gln Thr Ile Ser Val Lys
        195                 200                 205

Gln Asp Ile Val Ile Ala Ala Ala Gly Gln Ala Met Met Ile Lys Gly
```

-continued

```
            210                 215                 220
Asp Trp Xaa Lys Gln Lys Arg Asn Xaa Ile Xaa Val Gly Thr Ile His
225                 230                 235                 240

Arg Arg Pro Thr Arg Ile Trp Val Lys Ser Leu Xaa Val Val Leu Xaa
            245                 250                 255

Xaa Thr Ser Xaa Val Thr Asp Arg Pro Gly Xaa Ser Ala Ile Leu Xaa
            260                 265                 270

Phe Leu Lys Lys Gly Xaa Xaa Lys Xaa Xaa His Asp Ser Xaa Ile Glu
            275                 280                 285

Gly
```

What is claimed is:

1. An isolated polynucleotide comprising:
   (a) a nucteotide sequence encoding a polypeptide having methylenetetrahydrofolate dehydrogenase activity, wherein the polypeptide has an amino acid sequence of at least 90% sequence identity, based on the Clustal method of alignment with pairwise alignment default parameters of KTUPLE=1, GAP PENALTY=3, WINDOW=5 and DIAGONALS SAVED=5, when compared to SEQ ID NO:16, or
   (b) a complement of the nucleotide sequence of (a), wherein the complement and the nucleotide sequence consist of the same number of nucleotides and are 100% complementary.

2. The polynucleotide of claim 1, wherein the amino acid sequence of the polypeptide has at least 95% sequence identity, based on the Clustal method of alignment with the pairwise alignment default parameters, when compared to SEQ ID NO:16.

3. The polynucleotide of claim 1, wherein the amino acid sequence of the polypeptide comprises SEQ ID NO:16.

4. The polynucleotide of claim 1 wherein the nucleotide sequence comprises SEQ ID NO:15.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A plant comprising the recombinant DNA construct of claim 6.

10. A seed comprising the recombinant DNA construct of claim 6.

* * * * *

UNITED STATES PATENT AND TRADEMARK OFFICE
CERTIFICATE OF CORRECTION

PATENT NO. : 6,680,428 B2
APPLICATION NO. : 09/903814
DATED : January 20, 2004
INVENTOR(S) : Falco et al.

It is certified that error appears in the above-identified patent and that said Letters Patent is hereby corrected as shown below:

In Column 19, line 2, replace "MEGALIGNTM" with --MEGALIGN$^{TM}$--.

In Column 21, line 48, replace "MEGALIGNTM" with --MEGALIGN$^{TM}$--.

Top of columns 27 and 28, Sequence Listing section: please delete entire section beginning at top of columns 27 and 28 through top of columns 55 and 56 and replace with Amended Sequence Listing filed on January 2, 2003 and acknowledged April 8, 2003.

Last page of patent, claims section, claim 1, column 55, line 20: replace "nucteotide" with --nucleotide--.

Signed and Sealed this

Fourteenth Day of November, 2006

JON W. DUDAS
*Director of the United States Patent and Trademark Office*

SEQUENCE LISTING

<160> NUMBER OF SEQ ID NOS: 22

<210> SEQ ID NO 1
<211> LENGTH: 560
<212> TYPE: DNA
<213> ORGANISM: Zea mays
<220> FEATURE:
<221> NAME/KEY: unsure
<222> LOCATION: (442)
<221> NAME/KEY: unsure
<222> LOCATION: (520)

<400> SEQUENCE: 1

| | |
|---|---|
| gctccccaca ggcccacacc aaccaactct ctctgcctcg gtccctccgc ccgtacgcgc | 60 |
| gacgagagac acgatgcggc ggtccctccc cctcctcctc gcgcggcagg tggcgcggca | 120 |
| gcggcggctg agcaacgtgc cggagtccac cgtctacggg ggcccacgcc cgcaggagtc | 180 |
| ctcggcggcg cggcgcgtga cggtgaccac actccgtggg aagcaccgcc gcggggagcc | 240 |
| catcaccgtc gtcaccgcct acgactaccc ctcggcggtc cacgtcgact ccgccggcat | 300 |
| cgacgtctgc ctcgtcgggg actccgccgc catggtcgtc cacggccacg acaccacgct | 360 |
| ccccatcacg ctcgacatca tgctcgaagc actgccgcgc cgttggcccg gggcgcgccg | 420 |
| cgcccgctcc tcgtcgggga tntccaattc ggctgctaca atccttcggc gccaagctgt | 480 |
| tgattaaccg ttaaggtctc aaggaagtgg atggtgcatn aactggaagg ggtgccatca | 540 |
| ggttattgaa caaaggtatt | 560 |

<210> SEQ ID NO 2
<211> LENGTH: 375
<212> TYPE: PRT
<213> ORGANISM: Zea mays

<400> SEQUENCE: 2

Pro Thr Gly Pro His Gln Pro Thr Leu Ser Ala Ser Val Pro Pro Pro
 1               5                  10                  15

Val Arg Ala Thr Arg Asp Thr Met Arg Arg Ser Leu Pro Leu Leu Leu
            20                  25                  30

Ala Arg Gln Val Ala Arg Gln Arg Arg Leu Ser Asn Val Pro Glu Ser
        35                  40                  45

Thr Val Tyr Gly Gly Pro Arg Pro Gln Glu Ser Ser Ala Ala Arg Arg
    50                  55                  60

Val Thr Val Thr Thr Leu Arg Gly Lys His Arg Arg Gly Glu Pro Ile
65                  70                  75                  80

Thr Val Val Thr Ala Tyr Asp Tyr Pro Ser Ala Val His Val Asp Ser
                85                  90                  95

Ala Gly Ile Asp Val Cys Leu Val Gly Asp Ser Ala Ala Met Val Val
            100                 105                 110

His Gly His Asp Thr Thr Leu Pro Ile Thr Leu Asp Ile Met Leu Glu
        115                 120                 125

His Cys Arg Ala Val Ala Arg Gly Ala Pro Arg Pro Leu Leu Val Gly
    130                 135                 140

Asp Leu Pro Phe Gly Cys Tyr Glu Ser Ser Ala Ala Gln Ala Val Asp
145                 150                 155                 160

Ser Ala Val Arg Val Leu Lys Glu Gly Gly Met Asp Ala Ile Lys Leu
                165                 170                 175

Glu Gly Gly Ala Pro Ser Arg Ile Thr Ala Ala Lys Ala Ile Val Glu